United States Patent
Thompson et al.

[11] Patent Number: 6,056,766
[45] Date of Patent: May 2, 2000

[54] STABILIZED TROCAR, AND METHOD OF USING SAME

[76] Inventors: Ronald J. Thompson, 110 Stanbery Ridge, Ft. Thomas, Ky. 41075; Jack B. Stubbs, 4266 Laura Marie Dr., Waynesville, Ohio 45068

[21] Appl. No.: 09/094,305

[22] Filed: Jun. 9, 1998

[51] Int. Cl.⁷ .................................................. A61B 17/34
[52] U.S. Cl. ............................................ 606/185; 606/108
[58] Field of Search ................................. 606/185, 108, 606/198, 174, 176, 184; 604/164, 165, 174, 175

[56] References Cited

U.S. PATENT DOCUMENTS

| | | |
|---|---|---|
| D. 358,209 | 5/1995 | Petruschke et al. . |
| 4,762,519 | 8/1988 | Frimberger . |
| 4,826,481 | 5/1989 | Sacks et al. . |
| 4,869,717 | 9/1989 | Adair . |
| 5,002,557 | 3/1991 | Hasson . |
| 5,066,280 | 11/1991 | Braithwaite . |
| 5,112,310 | 5/1992 | Grobe . |
| 5,116,353 | 5/1992 | Green . |
| 5,122,122 | 6/1992 | Allgood ................................. 604/174 |
| 5,152,749 | 10/1992 | Giesy et al. . |
| 5,158,543 | 10/1992 | Lazarus . |
| 5,167,627 | 12/1992 | Clegg et al. . |
| 5,176,697 | 1/1993 | Hasson et al. . |
| 5,215,526 | 6/1993 | Deniega et al. . |
| 5,271,380 | 12/1993 | Riek et al. . |
| 5,300,036 | 4/1994 | Mueller et al. . |
| 5,318,585 | 6/1994 | Guy et al. . |
| 5,334,150 | 8/1994 | Kaali . |
| 5,336,176 | 8/1994 | Yoon ................................. 604/174 |
| 5,338,302 | 8/1994 | Hasson . |
| 5,342,382 | 8/1994 | Brinkerhoff et al. . |
| 5,343,874 | 9/1994 | Picha et al. . |
| 5,348,541 | 9/1994 | Lyell . |
| 5,366,445 | 11/1994 | Haber et al. . |
| 5,370,625 | 12/1994 | Shichman . |
| 5,399,167 | 3/1995 | Deniega . |
| 5,407,427 | 4/1995 | Zhu et al. . |
| 5,431,638 | 7/1995 | Hennig et al. ........................... 604/264 |
| 5,431,676 | 7/1995 | Dubrul et al. . |
| 5,454,791 | 10/1995 | Tovey et al. . |
| 5,514,091 | 5/1996 | Yoon ........................................ 604/101 |
| 5,645,556 | 7/1997 | Yoon ........................................ 606/185 |
| 5,690,663 | 11/1997 | Stephens . |
| 5,690,664 | 11/1997 | Sauer et al. . |
| 5,697,946 | 12/1997 | Hopper et al. ........................... 606/185 |
| 5,707,362 | 1/1998 | Yoon . |
| 5,713,869 | 2/1998 | Morejon . |
| 5,725,553 | 3/1998 | Moenning . |
| 5,807,338 | 9/1998 | Smith et al. ............................. 604/164 |
| 5,843,115 | 12/1998 | Morejon . |

OTHER PUBLICATIONS

Brochure: Endopath, Tristar Blunt Tip Surgical Trocar, by Ethicon Endo–Surgery, a Johnson & Johnson company, Cincinnati, OH; 1994.

Brochure: Flexipath, Flexible Surgical Trocar, by Ethicon Endo–Surgery, a Johnson & Johnson company, Cincinnati, OH; 1993.

*Primary Examiner*—Michael Buiz
*Assistant Examiner*—Jonathan D. Goldberg
*Attorney, Agent, or Firm*—Dinsmore & Shohl LLP

[57] ABSTRACT

A trocar employing an internal stabilizer and an optional external stabilizer is provided. The internal stabilizer is passed through the tissue wall along with the cannula, with the internal stabilizer in a retracted position. Once the cannula has been extended into the anatomical cavity, the stabilizer returns to its normal, extended position. Movement of the stabilizer between its retracted and extended positions is effected by advancement and retraction of the obturator. A method of inserting the trocar cannula is also provided.

21 Claims, 13 Drawing Sheets

6,056,766

STABILIZED TROCAR, AND METHOD OF USING SAME

BACKGROUND OF THE INVENTION

1. Field of the Invention

The present invention is directed towards a stabilized trocar, as well as a method of using the same. More particularly, the present invention provides a trocar having a stabilizer positioned adjacent its distal end, wherein the stabilizer, in its deployed position, will prevent premature dislodgement or removal of the trocar cannula from a tissue wall through which it extends.

2. Description of Related Art

Various medical procedures require the penetration of tissue to provide access to the interior of a patient's body. This is particularly true, for example, of endoscopic procedures wherein an opening in tissue must first be created to provide access to anatomical cavities or other internal structures. As used herein, "endoscopic" refers to procedures which employ tubular optical instruments (i.e., endoscopes) which are inserted into a patient to provide vision therein. The endoscope also typically has a hollow central passageway through which other instruments may be inserted into the patient. The term "endoscopic" is generic to, and therefore includes, terms such as "laparoscopic" and "arthroscopic" which refer to the use of an endoscope in a particular region of the body.

Whether the device being inserted into an anatomical cavity of a patient is an endoscope (through which other instruments may thereafter be inserted) or a simple surgical instrument such as a grasper, a cannula is first passed through the tissue wall into the anatomical cavity. Thereafter, the endoscope or other surgical instrument is inserted through the cannula into the anatomical cavity. In this manner, the cannula provides a passageway which will remain open during the surgical procedure, thereby providing the needed access to the anatomical cavity.

One commonly-employed instrument for penetrating tissue and positioning a cannula therein is referred to as a "trocar." Trocars generally comprise a cutting assembly (or obturator) and an outer cannula (also referred to as the trocar tube or sleeve). The cannula is positioned against the patient's skin, and the cutting assembly is positioned within the interior of the cannula. The sharp distal end of the cutting assembly is then urged through the skin until it enters the anatomical cavity being penetrated. The cannula is then urged through the tissue opening created by the cutting assembly, and the cutting assembly is thereafter withdrawn from the cannula. The cannula remains in place, and provides a passageway through which access to the anatomical cavity is provided.

The typical cannula, however, does not include any means for ensuring that the cannula remains in place during the medical procedures. Frequently, the cannula will become dislodged, thereby requiring re-insertion or repositioning. While the cannula may become entirely dislodged such that it falls out of the tissue wall, more often the cannula will only become partially dislodged from the tissue opening such that the tip (or distal end) of the cannula is positioned between tissue layers of the tissue wall through which it extends (rather than within the anatomical cavity). If the surgeon is unaware of this dislodgment, the medical instruments inserted through the cannula may become lost between the tissue layers or even in the wrong anatomical cavity. While usually merely a nuisance to the surgeon, cannula dislodgment can lead to serious patient injury.

Various apparatus and techniques for preventing cannula dislodgment have been developed, including those shown in U.S. Pat. Nos. 5,707,362, 5,407,427, 5,713,869, and 5,725,553. Unfortunately, each of these previous attempts suffers from numerous drawbacks, such as difficulty of operation, ineffectiveness, or even risk of patient injury. Thus, there is a need for apparatus and methods which provide effective cannula stabilization.

BRIEF DESCRIPTION OF THE DRAWINGS

While the specification concludes with claims particularly pointing out and distinctly claiming applicants' invention, it is believed that the same will be better understood from the following description taken in conjunction with the accompanying drawings in which:

SUMMARY OF THE PREFERRED EMBODIMENTS

Figure 1:
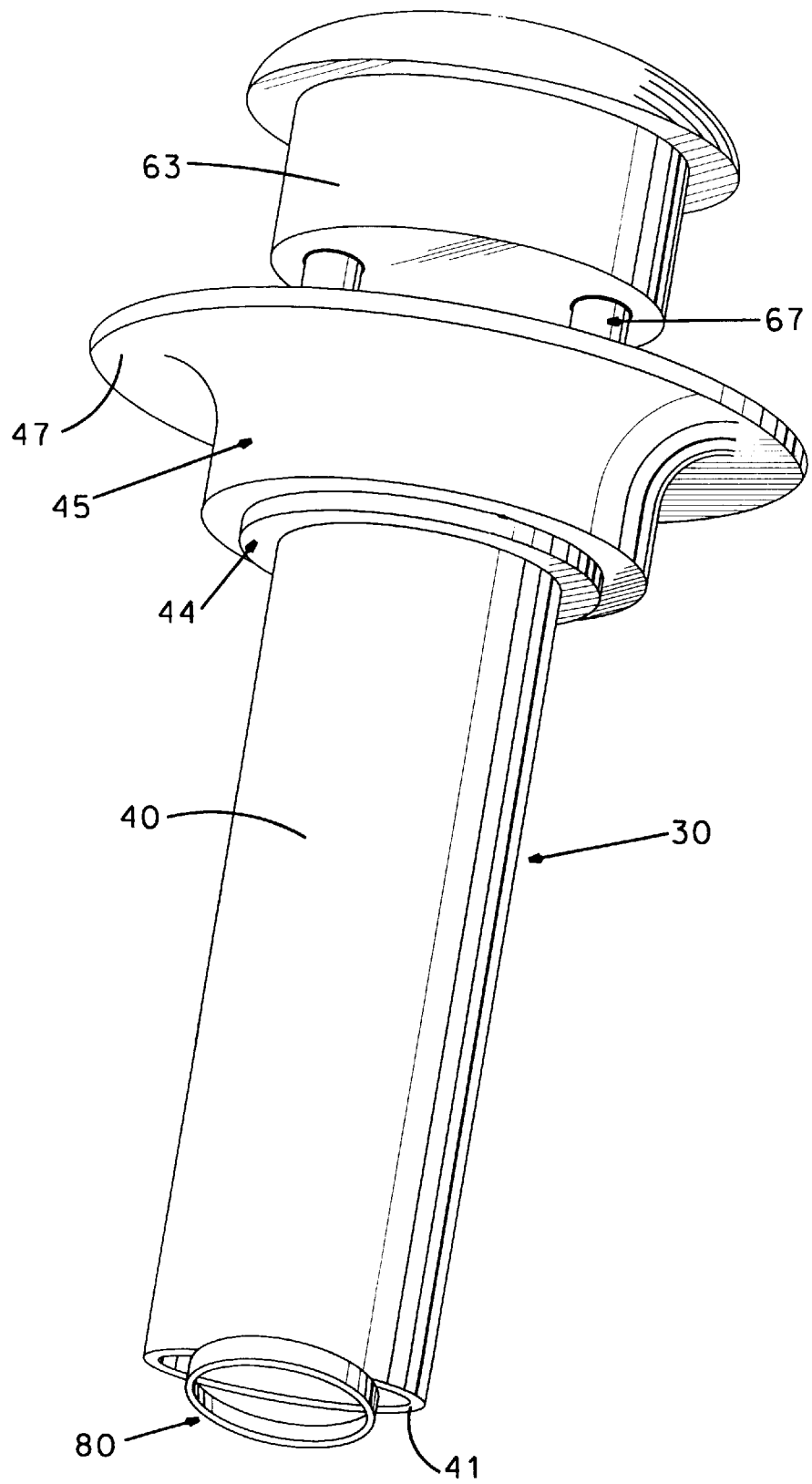
FIG. 1 is a perspective view of an apparatus according to one embodiment of the present invention.

It is an object of the present invention to provide a trocar which includes an internal stabilizer for preventing dislodgment of the trocar cannula.

It is another object of the present invention to provide a trocar which also may include an external stabilizer (or retention member) which bears against the external surface of the tissue wall through which the trocar cannula has been inserted.

It is yet another object of the present invention to provide a method of inserting a trocar cannula through a tissue wall into an anatomical cavity.

The foregoing objects, and numerous others, may be provided by a method of inserting a cannula through a tissue wall into an anatomical cavity, comprising:

(a) providing a trocar having a cannula and an obturator, the cannula having:
   a sleeve having a distal end and a longitudinal axis; and
   a stabilizer positioned adjacent the distal end of the sleeve, the stabilizer movable between extended and retracted positions;
   the obturator positioned at least partially within the sleeve, and having a distal end configured for penetrating tissue;

(b) positioning the distal end of the obturator adjacent a tissue wall to be penetrated;

(c) advancing the distal end of the obturator and the cannula sleeve through the tissue wall into the anatomical cavity, with the distal end of the obturator extending beyond the distal end of the sleeve and the stabilizer in the retracted position; and (c) withdrawing the obturator away from the distal end of the sleeve, the withdrawal causing the stabilizer to move from the retracted position to the extended position, such that the stabilizer prevents removal of the cannula from the anatomical cavity.

When the stabilizer is in its extended position, at least a portion of the stabilizer extends beyond the outer circumference of the distal end of the cannula sleeve. In other words, the extended stabilizer (also referred to as undeformed or in its second position) has a maximum cross-sectional diameter which is greater than the corresponding diameter of the distal end of the cannula sleeve. The term "corresponding diameter" simply means that the diameter of the distal end of the sleeve is measured along a line which is parallel to the line defining the maximum cross-sectional diameter of the stabilizer. In contrast, when the stabilizer is in its retracted position (also referred to as its deformed or first position), the stabilizer does not extend substantially beyond the outer circumference of the distal end of the cannula sleeve. Thus, in a preferred embodiment, when the stabilizer is in its deformed position, the maximum cross-sectional diameter of the stabilizer is substantially equal to or less than the corresponding diameter of the distal end of the cannula sleeve. Preferably, advancement of the obturator results in the desired deformation of the stabilizer to its deformed (or retracted) position, and even more preferably the obturator accomplishes this by passing through the interior of the stabilizer such that the obturator deforms the stabilizer to a configuration which allows the obturator to pass therethrough.

The cannula further may comprise a spring-biased retention member spaced away from the distal end of the cannula sleeve, the retention member spring-biased towards the distal end of the cannula sleeve. The retention member therefore comprises a second, external stabilizer, and may be provided as the cannula housing (or a portion thereof). In a preferred embodiment, the cannula includes upper and lower housings, and the lower housing is spring-biased towards the first stabilizer (therefore providing the "retention member"). Preferably, the lower housing is selectively spring-biased such that the spring-biasing is activated only upon withdrawal of the obturator away from the distal end of the sleeve. The lower housing is preferably configured such that, upon activation of the spring-biasing, the lower housing (or retention member) is urged against the exterior of the tissue wall through which the cannula has been inserted. Additionally, the first stabilizer may comprise an elliptical member which extends away from the distal end of the sleeve.

The present invention also provides a trocar comprising:

(a) a cannula having a distal end, a first stabilizer positioned adjacent the distal end of the cannula, and a second stabilizer spaced away from the distal end;

wherein the cannula may be inserted through a tissue wall in order to provide operative access to an underlying anatomical cavity, with the first stabilizer positioned adjacent the tissue wall within the anatomical cavity and the second stabilizer positioned adjacent the tissue wall outside of the anatomical cavity. Preferably, the first and second stabilizers are spring-biased towards each other such that the tissue wall in which the cannula may be positioned will be held (i.e., slightly compressed) between the first and second stabilizers. The trocar also preferably includes an obturator, and it is configured such that advancement of the obturator towards the distal end of the cannula deforms the first stabilizer to a retracted position which facilitates passage of the distal end of the cannula through a tissue wall. Withdrawal of the obturator away from the distal end of the cannula allows the first stabilizer to return to its extended, undeformed position which prevents removal of the cannula from a tissue wall through which it extends.

DETAILED DESCRIPTION OF THE INVENTION

The present invention provides apparatus and methods for penetrating tissue and creating an opening therein, particularly for creating a tissue opening which provides access to an anatomical cavity within a patient (both human and animal). More particularly, the apparatus and methods of the present invention may be employed to create a tissue opening in which a cannula is positioned, thereby providing a channel through which other instruments may be inserted (e.g., and endoscope, a surgical grasper, etc.) into the patient's body. When used in this manner, the apparatus of the present invention generally comprises a trocar assembly which includes the cannula which is positioned within the tissue opening.

As used herein, the term "anatomical cavity" refers to any actual or potential space within a patient, including, for example, the abdominal cavity (both intra- and extra-peritoneal), the thoracic cavity, organs, lumens, and even potential spaces (such as those often accessed during arthroscopic or laparoscopic procedures; for example, the space of Retzius). The term "tissue wall" generally refers to the layer of tissue overlying the anatomical cavity being accessed. For example, when the intra-peritoneal abdominal cavity is to be accessed, the tissue wall through which the cannula is inserted will include the outer layer of skin, the fascia, abdominal muscle, any layers of fat which are present, and the peritoneum.

Unlike prior art trocars, the apparatus of the present invention employs a cannula stabilizer which, when deployed within the anatomical cavity, prevents inadvertent removal or dislodgement of the cannula from the anatomical cavity into which it extends. In addition, a preferred embodiment of the trocar of the present invention also includes a spring-biased housing which bears against the outer surface of the tissue wall after the cannula has been inserted, thereby providing external cannula stabilization. In this manner, the tissue wall surrounding the opening therein will be compressed between the internal stabilizer and the spring-biased housing (the "second" stabilizer), thereby maintaining the cannula at the proper location.

FIG. 1 is a perspective view of a stabilized trocar assembly 30 according to one embodiment of the present invention. Like most trocars, that shown in FIG. 1 comprises a cannula which includes a cannula sleeve 40, and an upper housing 45 having a diameter greater than that of sleeve 40. An obturator (or cutting blade assembly) 60 is positioned within cannula sleeve 40. Obturator 60 is not visible in FIG. 1, since it is in its retracted position completely within sleeve 40. Unlike the prior art, trocar assembly 30 of the present invention includes a cannula stabilizer 80 positioned adjacent distal end 41 of sleeve 40. As used herein, "adjacent" means at or next to, and therefore stabilizer 80 is shown immediately next to distal end 41. It will be understood, however, that stabilizer 80 may even be provided on sleeve 40, coextensive with, or even above, distal end 41. Stabilizer 80 is shown in FIG. 1 in its extended/undeformed (or second) position whereat stabilizer 80 will prevent sleeve 40 from being withdrawn from a tissue opening through which sleeve 40 has been passed. As will be apparent from FIG. 1, in its undeformed position, stabilizer 80 has an outer diameter which is greater than the corresponding diameter of distal end 41 along the same axis. In other words, at least a portion of stabilizer 80 extends beyond the outer wall of distal end 41 of sleeve 40. As more fully described herein, stabilizer 80 is automatically deployed (i.e., advances to its extended or undeformed position) upon withdrawal of the obturator, thereby providing a simple mechanism for ensuring that the cannula sleeve will not be inadvertently dislodged during a surgical procedure.

Figure 13:
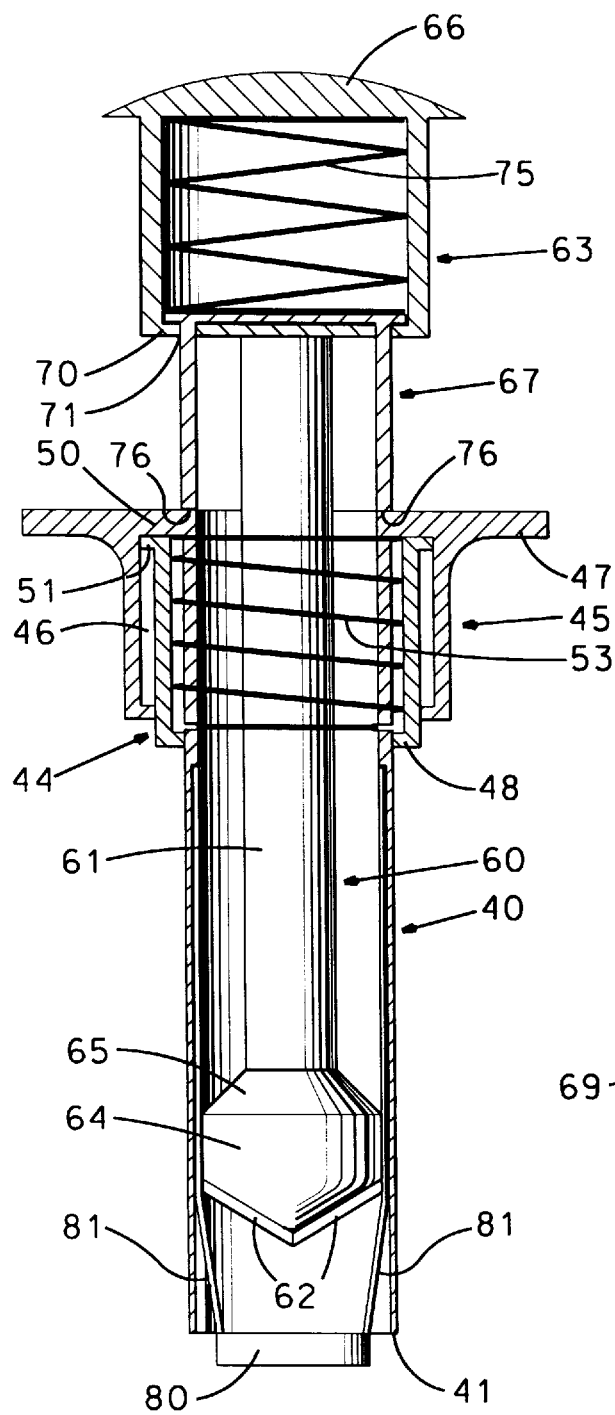
FIG. 13 is a partially cross-sectional view of an apparatus according to the present invention, wherein the obturator, stabilizer, and housing spring are not shown in cross-section.

Since the trocar of the present invention is similar in many respects to trocars currently employed by medical practitioners, structural details of the trocar will first be outlined without reference to either the upper or lower stabilizers of the present invention. Thus, FIG. 13 is a cross-sectional view of trocar assembly 30 of FIG. 1, wherein obturator (or cutting blade assembly) 60 and springs 53 and 75 are not shown in cross-section for purposes of clarity. Thus, it should be noted that, as described in further detail below, housing spring 53 extends about the circumference of cannula sleeve 40.

Figure 11:
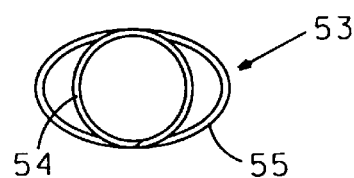
FIG. 11 is a bottom plan view of the housing spring.
Figure 12:
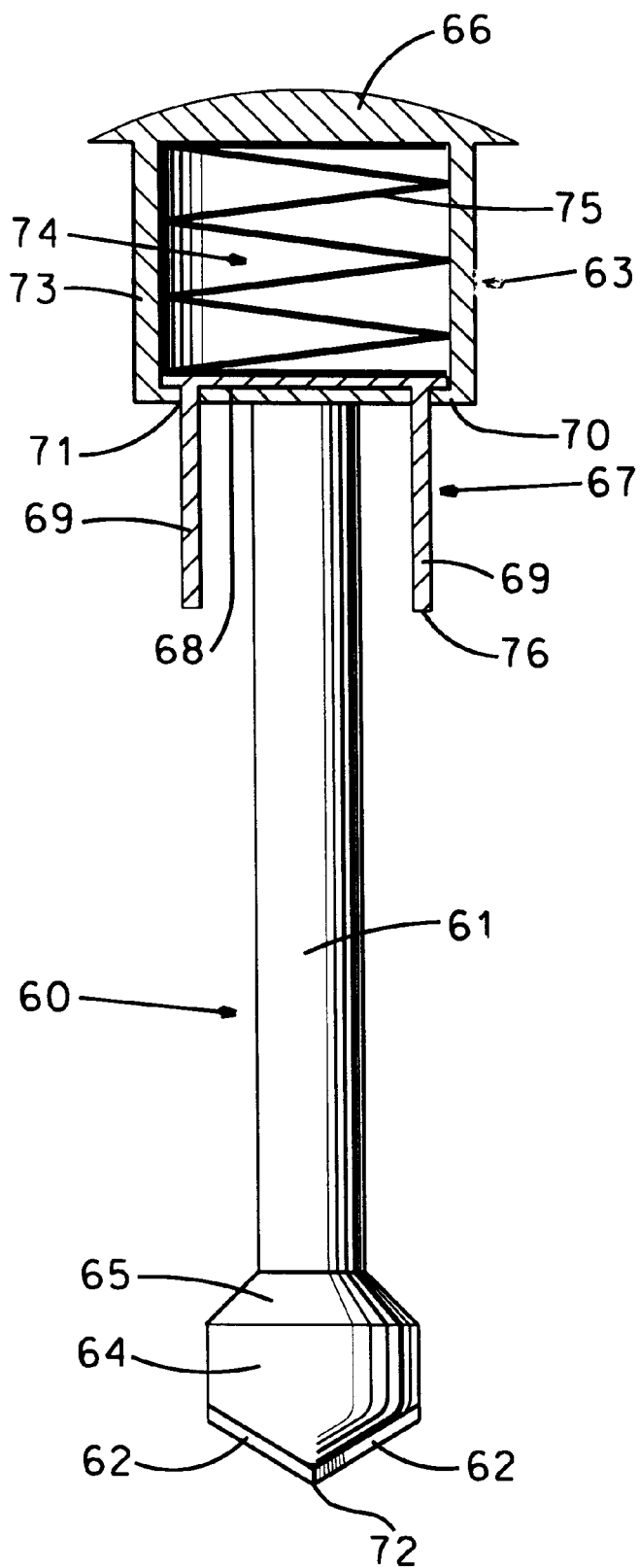
FIG. 12 is a side view of the obturator, cap member and thrust member according to the present invention, wherein the cap member and thrust member are shown in cross-section.

Trocar assembly 30 is shown in FIGS. 1 and 13 in its initial state, as the trocar would be provided to the surgeon. Thus, obturator 60 is shown in its retracted position wherein cutting blade 62 is safely positioned entirely within cannula sleeve 40. As more fully described herein, as cap member (or handle) 63 is compressed towards flange 47 of upper housing 45, obturator 60 will be urged downwardly such that cutting blade 62 will extend beyond distal end 41 of sleeve 40, as well as stabilizer 80 (as best seen in FIG. 11). With cutting blade 62 exposed (i.e., extending beyond the lower end of the trocar assembly), the cutting blade may be urged through the tissue wall of an anatomical cavity. Since the diameter of cannula sleeve 40 is only slightly greater than the diameter of distal end 64 of obturator 60, cannula sleeve 40 will follow cutting blade 62 through the tissue wall towards the anatomical cavity (as best seen in FIG. 12). Once cutting blade 62 and distal end 41 of cannula sleeve 40 have completely penetrated through the tissue wall into the anatomical cavity, cutting blade assembly 60 may be removed from the trocar assembly, thereby leaving cannula sleeve 40 in place. The hollow interior of cannula sleeve 40 thereafter provides operative access to the anatomical cavity into which distal end 41 of sleeve 40 extends.

Figure 5:
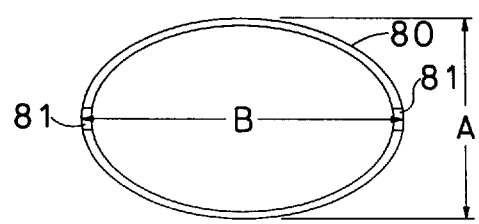
FIG. 5 is a top plan view of the stabilizer of FIG. 3.

As noted from FIGS. 5 and 13, the cannula portion of trocar assembly 30 generally comprises a cannula sleeve 40 having a lower (or distal end) 41. A housing is attached to sleeve 40 at its upper (or proximal end), and this housing should be larger than sleeve 40 such that it cannot penetrate the tissue wall. In the preferred embodiment shown in FIGS. 5 and 13, the housing comprises an upper housing portion 45 which is attached to, and is integral with, cannula sleeve 40. Of course other configurations well-known to those skilled in the art may be employed, such as a detachable upper housing 45. As will be more fully described below, a preferred embodiment of the present invention also includes a lower housing 44 which is selectively spring-biased towards distal end 41 of sleeve 40. In fact, the entire housing may be selectively spring-biased towards distal end 41, however a preferred embodiment includes upper and lower housings, only one of which may move with respect to cannula sleeve 40.

Figure 8:
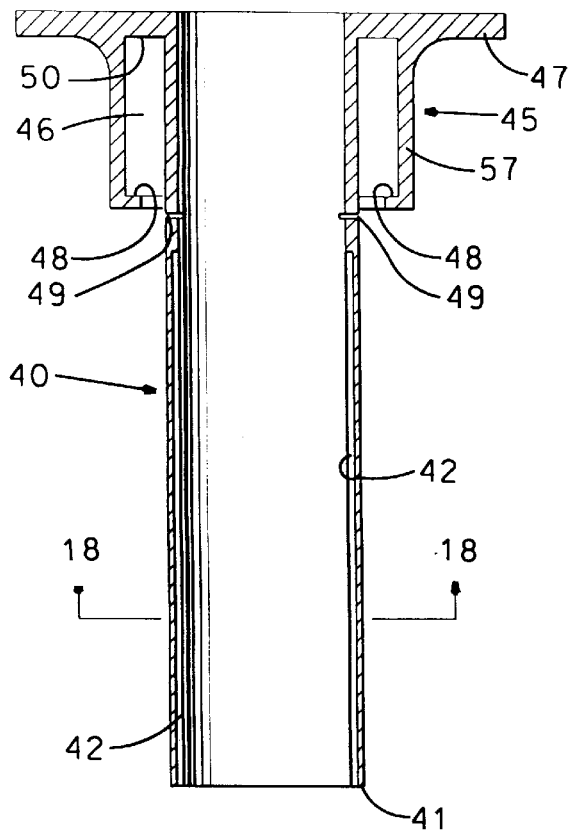
FIG. 8 is a cross-sectional view of the cannula.
Figure 21:
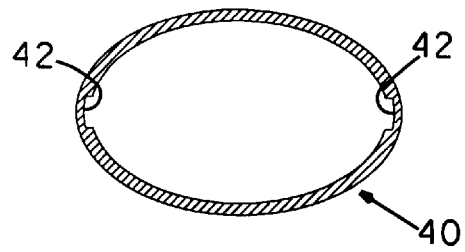
FIG. 21 is a cross-sectional view of the cannula sleeve of FIG. 8, taken along the line 18—18 thereof.

The length of cannula sleeve 40 should be selected such that its distal end can be readily positioned within the anatomical cavity being accessed with upper housing 45 spaced away from the outer surface of the tissue layer penetrated by the cannula (such as the skin). Of course, cannula sleeve 40 should also be hollow in order to provide an operative port which provides access to the anatomical cavity. In addition, it is also preferred that cannula sleeve 40 have a non-circular cross-sectional shape, more preferably an elliptical cross-sectional shape (as best seen in the cross-sectional view of FIG. 21). Cannula sleeve also has a pair of cutouts 42 extending lengthwise along the interior of sleeve 40 from distal end 41 towards housing 45. Cutouts 42 are provided on opposite sides of the interior wall of sleeve 40, preferably intersecting the major axis of the elliptical cross-sectional shape of sleeve 40. In other words, cutouts 42 extend along opposite sides of the interior surface of sleeve 40, upwardly away from distal end 41 and parallel to the longitudinal axis of sleeve 40. Preferably, cutouts 42 extend from distal end 41 to a point spaced below upper housing 45, as shown in FIG. 8. As more fully described below, cutouts 42 accommodate the mounting arms 81 of stabilizer 80.

Upper housing 45 is also preferably elliptical in cross-sectional shape, and has an outer wall 57 which extends around, and is spaced away from the outer wall of cannula sleeve 40. In this manner, an annular cavity 46 is provided between outer wall 57 of upper housing 45 and cannula sleeve 40. An inwardly extending lip 48 is provided at the lower end of outer wall 57. An upper wall 50 connects outer wall 57 of upper housing 45 to cannula sleeve 40, at the proximal end of sleeve 40. In this manner, upper wall 50 provides the uppermost wall of annular cavity 46. Upper housing 45 also includes an outwardly-extending flange 47 which extends radially outward from outer wall 57, as best seen in FIG. 8. Flange 47 provides a convenient means by which the medical practitioner may manipulate the trocar assembly of the present invention.

Figure 22:
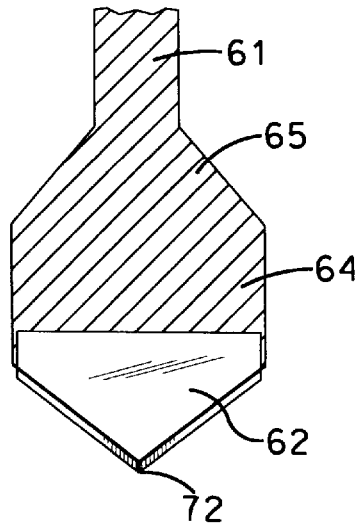
FIG. 22 is a cross-sectional view of the lower portion of the obturator.

FIGS. 12 and 22 depict preferred structural details for obturator 60, as well as cap member 63. Obturator 60 generally comprises an elongate shaft 61, a distal end portion 64 attached to the lower end of shaft 61, and one or more cutting blades 62 which extend away from distal end portion 64. In a preferred embodiment, cutting blade 62 has a pair of sharpened edges which taper upwardly away from pointed tip 72. Various other configurations for the cutting blade portion of obturator 60 may also be employed, however, such as the star- or triangular-shape cutting blades described in U.S. Pat. No. 5,215,526. In the embodiment of FIG. 22, cutting blade 62 may provided by a single, flat piece of metal having a pair of sharpened edges which meet at pointed tip 72. Cutting blade 62 may be secured to distal end portion 64 by a variety of means, such as molding distal end portion 64 about cutting blade 62. Of course distal end portion 64 and cutting blade 62 may even comprise a single, integral unit wherein distal end portion 64 merely tapers to one or more sharpened leading edges, similar to that shown in U.S. Pat. No. 5,116,353.

Distal end portion 64 of obturator 60 preferably has an elliptical cross-sectional shape which corresponds substantially in shape, and is slightly smaller than the interior of cannula sleeve 40. Thus, the maximum diameter of distal end portion 64 (i.e., across the major axis of its elliptical cross-section) should be only slight less than the maximum interior diameter of cannula sleeve 40 (i.e., across its major cross-sectional axis). In this manner, distal end portion 64 of obturator 60 should readily slide within the interior of cannula sleeve 40 with minimal play.

Figure 7:
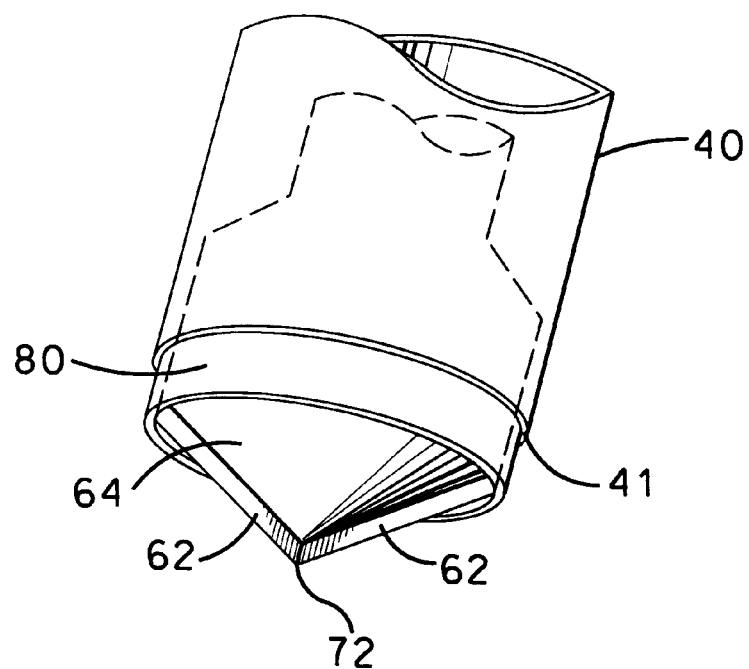
FIG. 7 is an end view of a portion of the trocar assembly according to the present invention.
Figure 23:
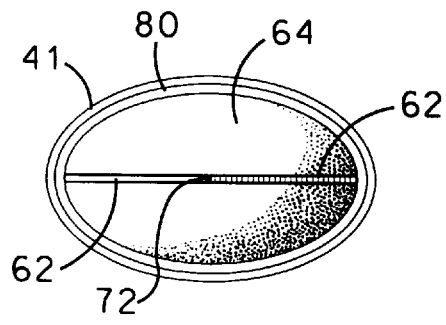
FIG. 23 is an end view of the trocar assembly shown in FIG. 15.

As best seen in FIGS. 7, 12, and 23, distal end portion 64 should also taper towards the sharpened leading edges of cutting blade 62 such that a smooth transition is provided between flat cutting blade 62 and elliptical distal end portion 64. In this manner, the lowermost portion of distal end 64 will essentially have an elliptical cone shape, and the uppermost portion of distal end 64 will have an elliptical cylinder shape. In this manner, as the sharp leading edges of cutting blade 62 penetrate through the tissue wall, distal end portion 64, since it tapers towards cutting blade 62, will gradually expand the tissue opening as it pass therethrough closely behind cutting blade 62. Since distal end portion 64 tapers to nearly the width of sleeve 40, this expansion of the tissue opening as distal end portion 64 is urged therethrough, will allow distal end 41 of cannula sleeve 40 to also pass through the tissue opening created by cutting blade 62, following closely behind distal end portion 64 of obturator 60. In fact, like most prior art trocars, cutting blade 62 and cannula sleeve 40 are urged through the tissue wall simultaneously, with sleeve 40 following closely behind cutting blade 62.

Conical taper portion 65 connects distal end 64 to obturator shaft 61. In fact, since obturator shaft 61 need not have an elliptical cross-sectional shape, conical taper portion 65 may have an elliptical cross-sectional shape where it meets distal end portion 64, and a circular cross-sectional shape where it meets shaft 61. Regardless, conical taper portion 65 provides a smooth transition between shaft 61, and the larger diameter distal end portion 64. In this manner, conical taper portion 65 provides a sloped shoulder which, as further described below, facilitates release of the spring-biased lower housing 44.

At its upper (or proximal) end, shaft 61 of obturator 60 is attached to cap member (or handle) 63. In fact, cap member 63 and obturator 60 may be formed as an integral unit. Cap member 63 generally comprises a hollow housing which includes circumferential sidewall 73, upper wall 66 and lower wall 70, all of which define an interior volume 74. Interior volume 74 is sized to accommodate a thrust member 67, as well as an obturator spring 75. It should be noted that upper wall 66 of cap member 63 may be formed separately such that thrust member 67 and obturator spring 75 may be easily positioned within interior volume 74, as shown, and upper wall 66 thereafter attached to cap sidewall 73.

Figure 14:
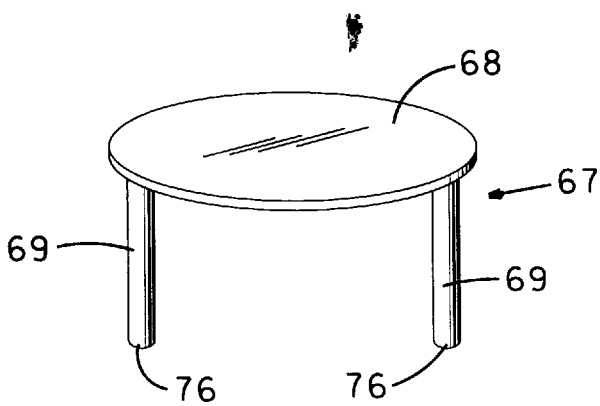
FIG. 14 is a perspective view of the thrust member.

As best shown in FIG. 14, thrust member 67 generally comprises a flat plate 68 having a shape corresponding to the cross-sectional shape of interior volume 74 of cap member 63 (e.g., elliptical or circular). Two or more thrust arms 69 extend downwardly away from plate 68 of thrust member 67. Thrust arms 69 are positioned and configured so as to be alignable with, and slidable within a pair of slots 71 provided in lower wall 70 of cap member 63. In this manner, thrust plate 68 of thrust member 67 may be positioned within interior volume 74 of cap member 63, with each thrust arm 69 extending downwardly through a slot 71 (as best seen in FIG. 12). Obturator spring 75 is positioned between plate 68 of thrust member 67, and upper wall 66 of cap member 63, and therefore will spring-bias thrust member 67 in the downward direction (i.e., towards cutting blade 62).

As best shown in FIG. 13, obturator 60 should be positioned within cannula sleeve 40 such that the lowermost ends of thrust arms 69 will bear against the upper surface of the cannula assembly. In the embodiment of FIG. 13, lower ends 76 of thrust arms 69 bear against upper wall 50 of upper housing 45. Since thrust member 67 is spring biased downwardly, cap member 63 is correspondingly biased in the upward direction since obturator spring 75 bears against upper wall 66 of cap member 63. Since obturator 60 is secured to cap member 63, obturator 60 will likewise be spring biased upwardly such that cutting blade 62 is normally safely maintained within cannula shaft 40, as shown in FIG. 13.

Figure 15:
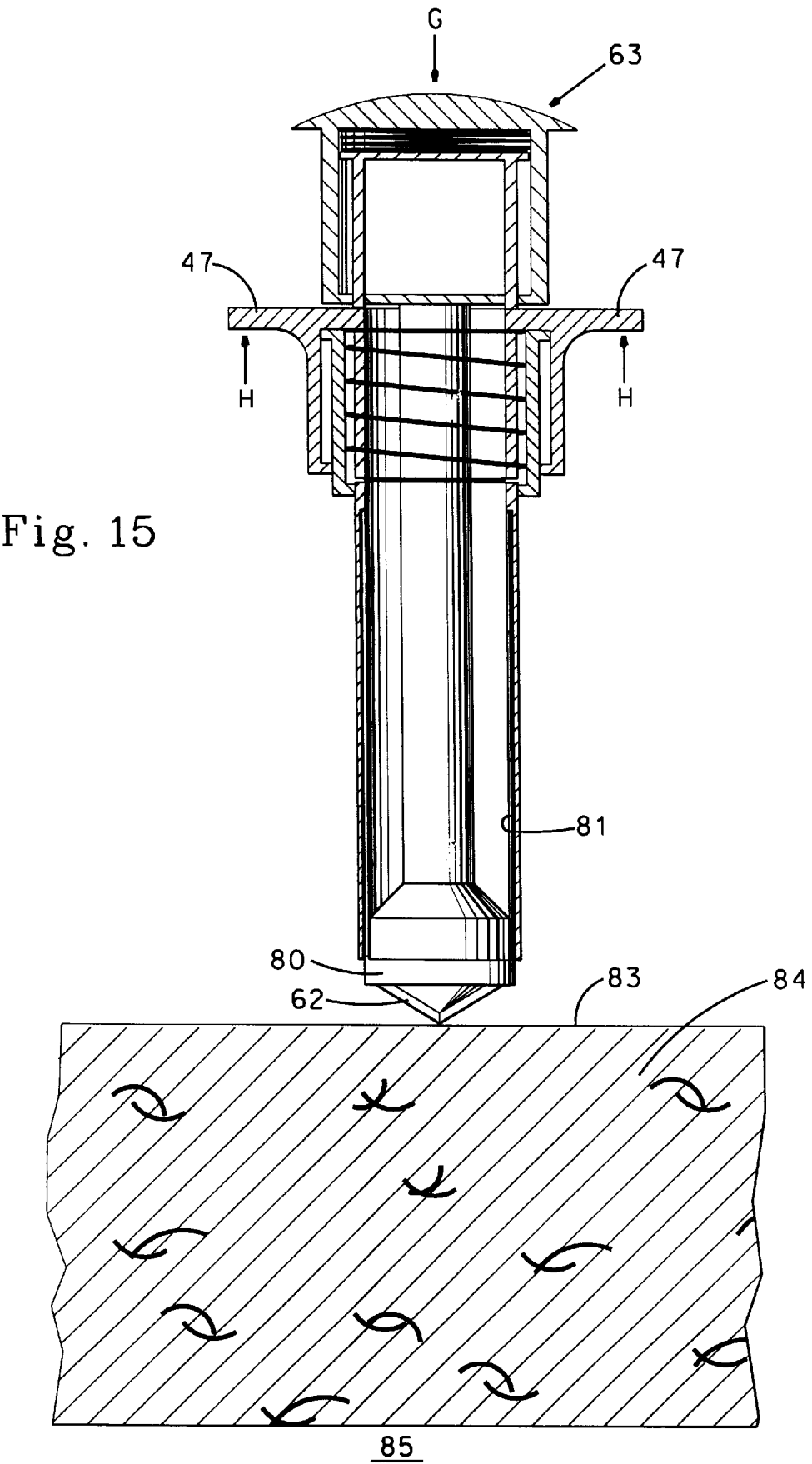
FIG. 15 is the same view as FIG. 13, wherein the cutting blade has been exposed and is positioned adjacent a tissue wall to be penetrated.

As best seen in FIG. 15, when a downward force G is applied to cap member 63, while an upward force H is applied against flange 47 of upper housing 45, obturator 60 will be urged downwardly such that cutting blade 62 will extend beyond distal end 41 of cannula 40, as well as beyond stabilizer 80. The extent of downward movement of cap member 63 and obturator 60, however, is limited since lower wall 70 of cap member 63 will contact upper wall 50 of upper housing 45. Preferably, cap member 63 and obturator 60 should be sized such that when cap member 63 has been depressed to its fullest extent, cutting blade 62 will extend just beyond stabilizer 80, as seen FIG. 15. It will also be noted that forces G and H may be readily applied by the medical practitioner grasping flange 47 with his fingers and exerting force G with the palm of the same hand bearing against cap member 63.

Figure 17:
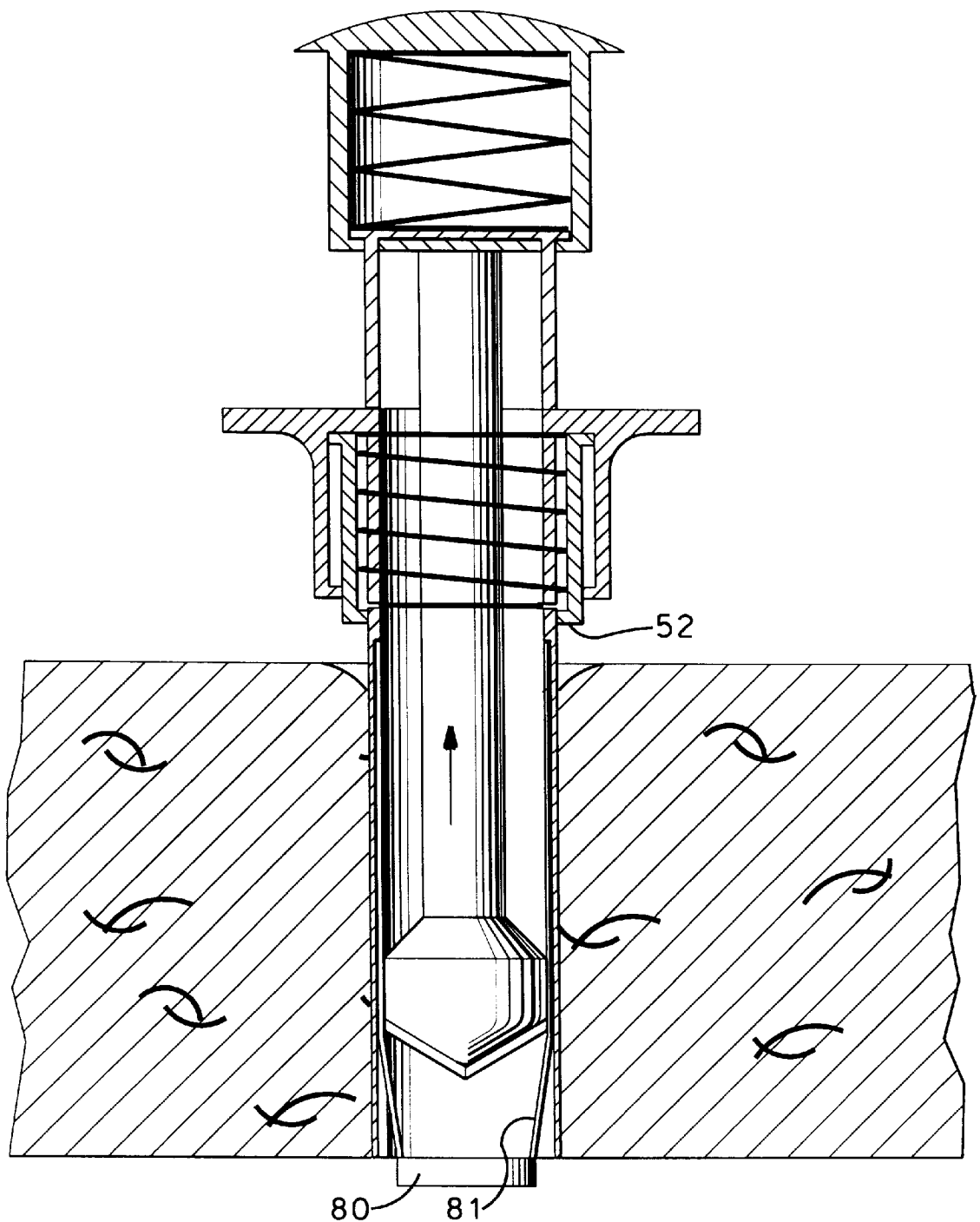
FIG. 17 is the same view as FIG. 16, wherein the obturator has been released.
Figure 18:
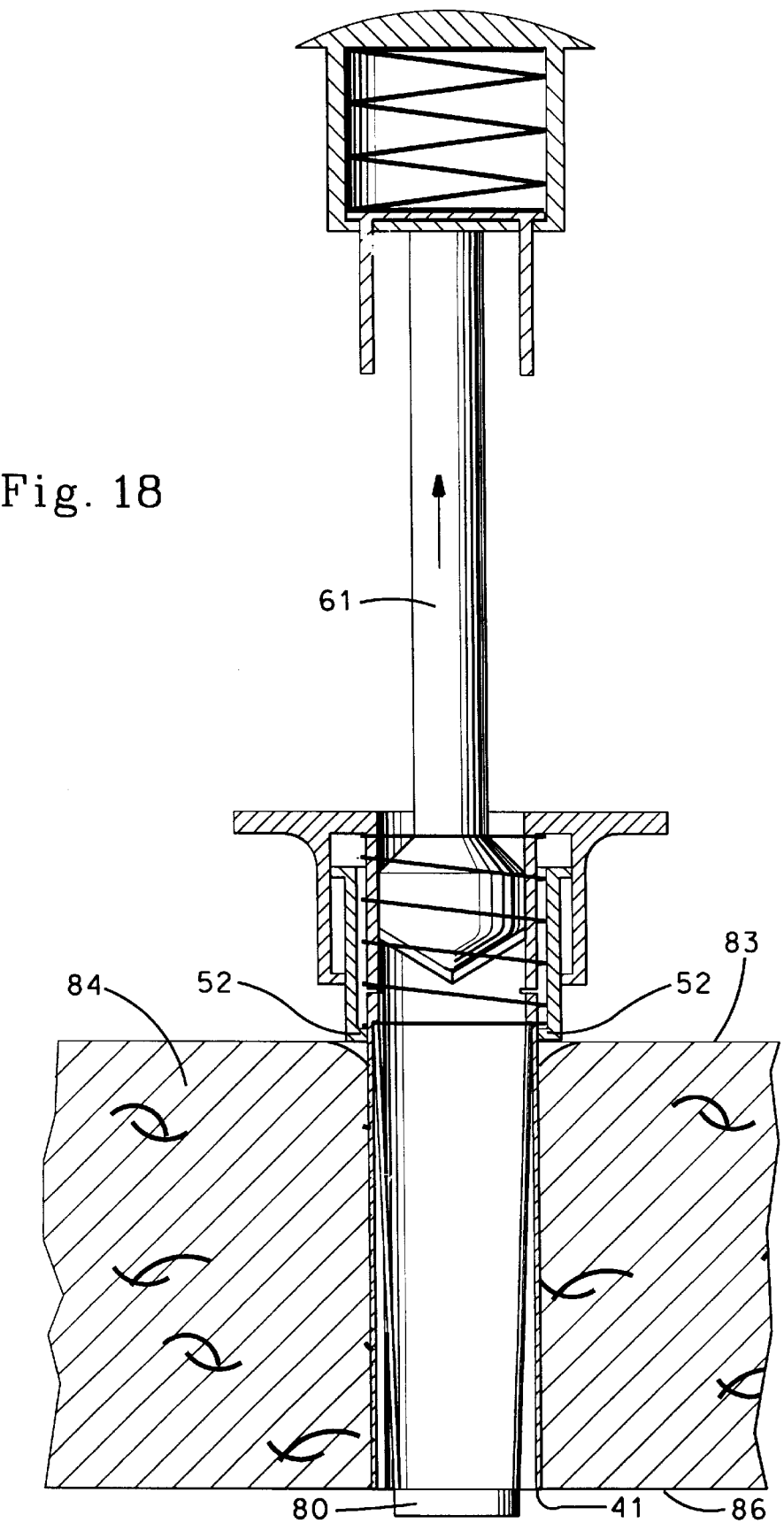
FIG. 18 is the same view as FIG. 17, wherein the obturator is being removed from the cannula sleeve.
Figure 19:
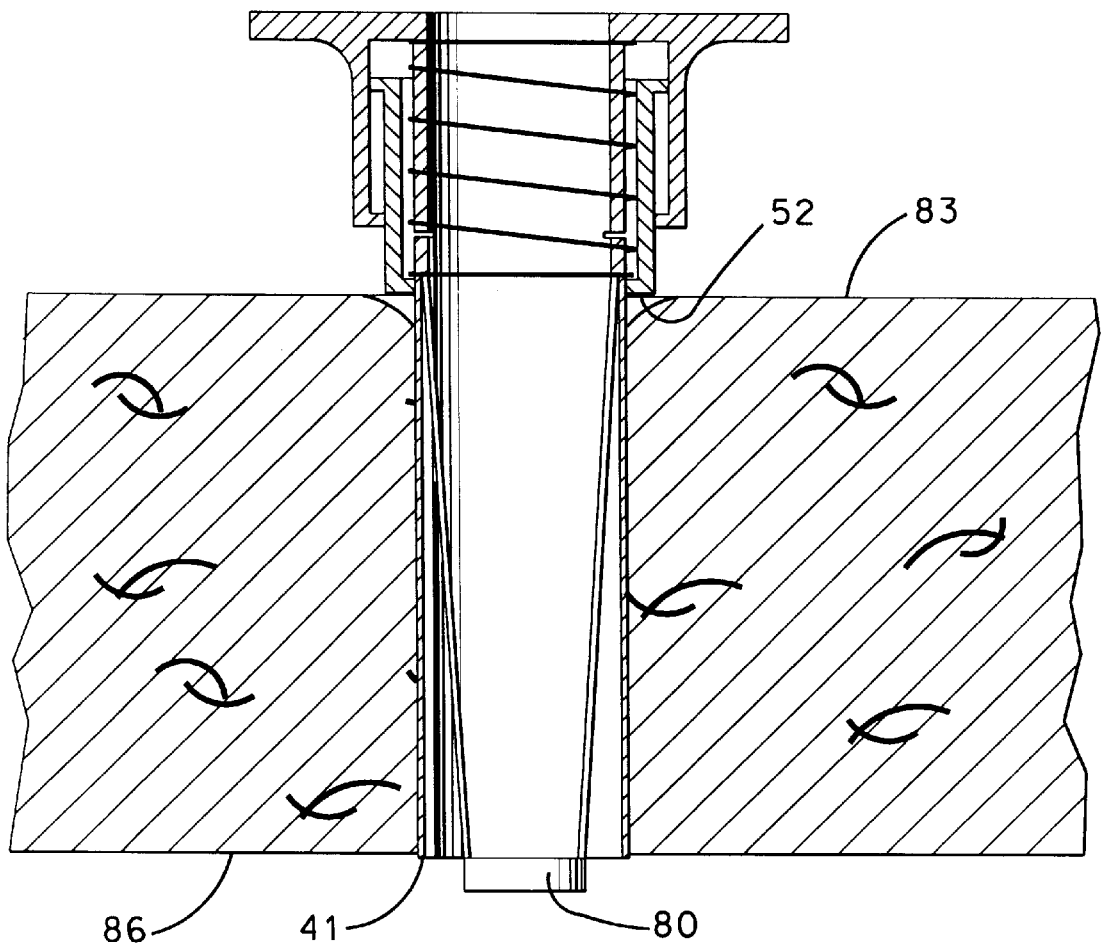
FIG. 19 is the same view of FIG. 18, wherein the obturator has been completely removed, and only the cannula remains in place.

Use of the trocar assembly of the present invention is straightforward. With reference to FIG. As is typical with trocar insertion, the medical practitioner will often first create a small incision in the outer layer 83 of the tissue wall 84 to be penetrated, particularly when this tissue wall includes an outer layer of skin 83. Thereafter, forces G and H will be applied to the assembly, as shown in FIG. 15, thereby exposing cutting blade 62. At the same time, the medical practitioner will urge cutting blade 62 against the tissue wall to be penetrated, and thereafter apply a downward force in order to urge cutting blade 62 through the tissue wall. Since cutting blade 62 extends nearly across the entire diameter of stabilizer 80 and distal end 41 of cannula sleeve 40, as cutting blade 62 is urged through the tissue wall, stabilizer 80 and cannula sleeve 40 will also pass through the tissue opening created by cutting blade 62. Once distal end 41 of cannula 40 has completely penetrated through the tissue wall into the anatomical cavity 85, forces G and H are removed. Upon removal of these forces, obturator spring 75 will urge cap member 63, and hence obturator 60, upwardly (as seen in FIG. 17). This results in cutting blade 62 being automatically retracted to its original position within cannula sleeve 40. Since obturator 60 and cap member 63 are not secured to the cannula, cap member 63 and obturator 60 may then be completely removed from the cannula, as shown in FIG. 18. This results in the cannula remaining in place, with cannula sleeve 40 extending completely through the tissue wall in order to provide operative access to the underlying anatomical cavity.

It should be noted at this point that the trocar assembly of the present invention may be employed with the backstop assembly described in Applicants' co-pending patent application Ser. No. 09/065,254, which was filed on Apr. 23, 1998, and which is incorporated herein by way of reference. In particular, the backstop lighted backstop assembly depicted in FIGS. 30–36 of that application may first be positioned within the anatomical cavity, and the trocar of the present invention thereafter driven through the tissue wall until cutting blade 62 meets the backstop. In this manner, over-penetration of the sharp cutting blade will be prevented.

Figure 2:
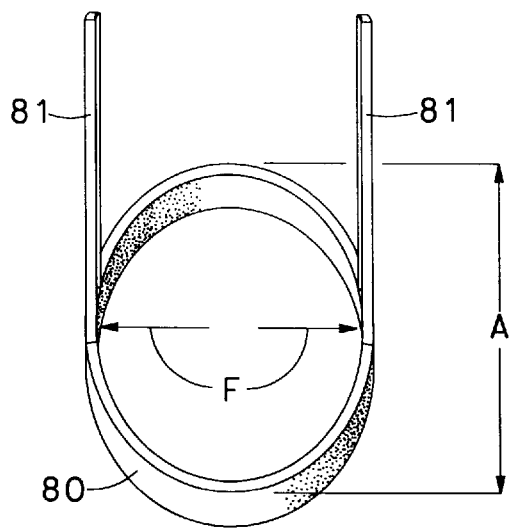
FIG. 2 is a perspective view of an elliptical stabilizer according to the present invention.

Although the above-described trocar can be effectively employed for proper positioning of a cannula in a tissue wall, particularly in conjunction with the backstop assembly of Applicants' co-pending application, the present invention also includes internal and external cannula stabilizers which may be employed alone or in conjunction with one another. FIG. 2 is a perspective view of first (or internal) stabilizer 80 of the present invention, wherein the stabilizer is shown in its extended/undeformed (or second) position. In a preferred embodiment, stabilizer 80 comprises an elliptical strip (i.e., an elliptical cylinder) of an elastic material. Preferably, stabilizer 80 is made from a material possessing shape memory, such that stabilizer 80 may be readily deformed, and will return to its extended position shown in FIG. 2 upon removal of the force causing the deformation. One preferred material for stabilizer 80 is a shape memory metal, such as nitinol. Although nitinol possesses significant shape memory, other types of metals possessing less memory may also be employed, such as stainless steel. Of course other materials, such as plastic, also possess some shape memory, and may therefore be used to produced stabilizer 80.

Figure 4:
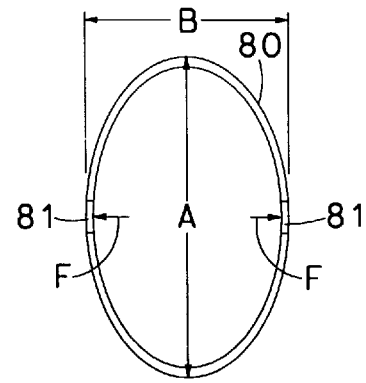
FIG. 4 is a top plan view of the stabilizer of FIG. 2.
Figure 3:
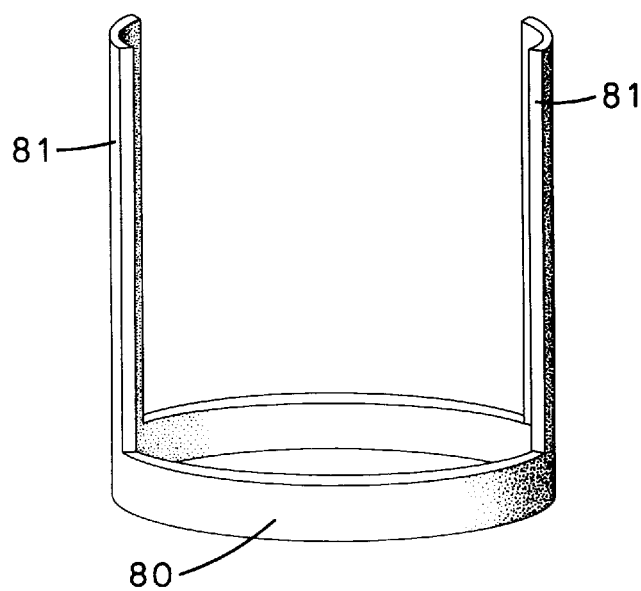
FIG. 3 is a perspective view of the stabilizer shown in FIG. 2, wherein the stabilizer has been deformed in order to allow cannula passage through tissue.

When stabilizer 80 is in its extended (or undeformed) position, the maximum diameter of stabilizer 80 corresponds to its major axis and is defined at A. The minimum diameter of stabilizer 80 when it is in its extended position is that defined by the minor axis of the elliptical cross-sectional shape. Since stabilizer 80 is preferably made from a flexible, shape memory material, a force F applied in the radially outward directions shown in FIG. 2 will cause stabilizer 80 to deform. When force F is applied in this manner, stabilizer 80 will be deformed to its retracted (or first) position, as shown in FIGS. 3 and 5. As will be apparent, the major and minor axis of elliptical stabilizer 80 are essentially switched. In other words, the maximum diameter of stabilizer 80 when it is in its deformed position (FIGS. 3 and 5) is positioned 90° from the location of the maximum diameter when stabilizer 80 is in its undeformed position (FIGS. 2 and 4). As more fully described below, stabilizer 80 protrudes beyond the outer circumference of distal end 41 of sleeve 40 only when in its undeformed position. When stabilizer 80 is in its deformed (or retracted) position, it will substantially not protrude beyond the outer circumference of distal end 41 of sleeve 40.

The relationship between the deformed and undeformed states of elliptical stabilizer 80 may also be better understood from the top plan views of FIGS. 4 and 5 which depict stabilizer 80 in its undeformed and deformed states, respectively. In other words, FIG. 4 is a top plan view of stabilizer 80 oriented in the manner shown in FIG. 2, while FIG. 5 is a top plan view of stabilizer 80 shown in its orientation of FIG. 3. When stabilizer 80 is in its undeformed state, as shown in FIG. 4, its maximum diameter A is defined by the major axis of the ellipse defined by stabilizer 80. The minor axis of the ellipse defines the minimum diameter B of stabilizer 80, as shown in FIG. 4. When a force F is applied from the interior of stabilizer 80 radially outward along minor axis B, as shown, elliptical stabilizer 80 will be deformed into the configuration shown in FIG. 5. Upon such deformation, the maximum diameter of stabilizer 80 is now defined at B, while the minimum diameter is defined at A. As will be more fully described below, the deformed (or first) position for stabilizer 80 shown in FIG. 5 allows for insertion of the trocar cannula through a tissue opening into the patient. In contrast, when stabilizer 80 is in its undeformed (or second) position shown in FIG. 4, stabilizer 80 will prevent withdrawal or inadvertent dislodgment of the trocar cannula from the patient.

As best seen in FIGS. 2 and 3, a pair of mounting arms 81 extend upwardly away from stabilizer 80. Mounting arms 81 can take a variety of configurations, and that shown is merely one presently contemplated embodiment. Mounting arms 81 generally comprise an elongate strip of material, and may comprise a shape memory metal such as that used for stabilizer 80. Although mounting arms 81 may each comprise a flat strip of material, it is preferred that mounting arms 81 have a slight curvature corresponding to the interior curvature of cutouts 42 within cannula sleeve 40. Various other configurations may be employed, however, since the mounting arms 81 merely provide a means for positioning stabilizer 80 adjacent distal end 41 of cannula sleeve 40.

Figure 6:
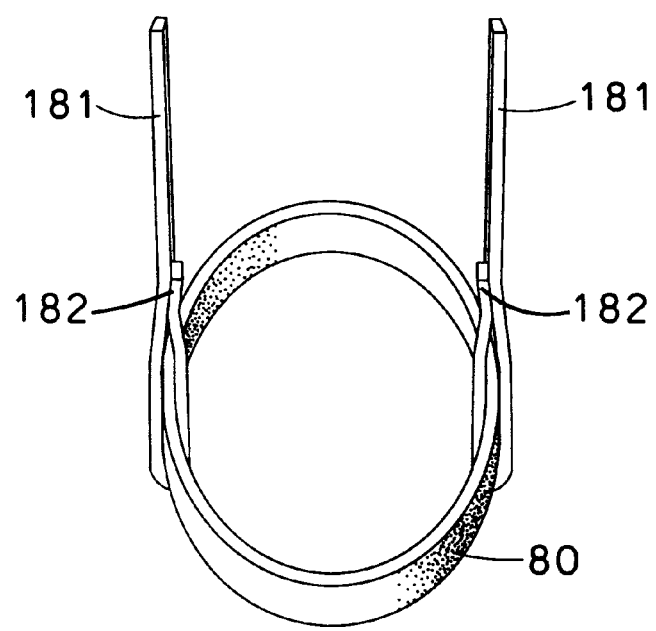
FIG. 6 is a perspective view of an alternative embodiment for the stabilizer used in the present invention.

Although stabilizer 80 and its accompanying mounting arms 81 may be cast or otherwise molded as a single, integral unit, FIG. 6 depicts an alternative embodiment which may be employed. Stabilizer 80 of FIG. 6 has the same configuration as that previously described. In the embodiment of FIG. 6, however, mounting arms 181 are formed separately from stabilizer 80 and each comprises a strip of material which is folded around stabilizer 80 on opposite sides thereof. The portion of each mounting arm 181 which is wrapped around stabilizer 80 may then be welded, bolted, glued or otherwise secured to itself above stabilizer 80. In this manner, each mounting arm 181 has a loop at its lower end through which stabilizer 80 passes. Stabilizer 80 at 182 need not be rigidly secured within the lower loop on each mounting arm 181, and may therefore be free to slide therein. In this manner, deformation of stabilizer 80 to the position shown in FIG. 3 will be facilitated. When the embodiment of FIG. 6 is employed, mounting arms 181 may be made from a variety of materials, including various metals or plastics, and, since mounting arms 181 are not integrally formed with stabilizer 80, they need not be of the same material as stabilizer 80.

As mentioned previously, cannula sleeve 40 preferably has a pair of cutouts extending upwardly from distal end 41 towards upper housing 45. Cutouts 42 should correspond in size and shape to mounting arms 81 (or 181) of stabilizer 80. In this manner, mounting arms 81 may be secured within cutouts 42 on sleeve 40 in order to position stabilizer 80 adjacent distal end 41 of cannula sleeve 40. In addition, since cutouts 42 are preferably positioned at opposite ends of the major axis of the elliptical cross-section of cannula sleeve 40, the minor axis of elliptical stabilizer 80 (when stabilizer 80 is in its undeformed state shown in FIG. 2) will be aligned with the major axis of the elliptical cross-section of cannula sleeve 40. In other words, the maximum diameter across stabilizer 80 will be located at a position which is 90° rotated from the maximum diameter across the cross-section of distal end 41 of cannula sleeve 40. In this manner, and as best shown in FIG. 1, stabilizer 80 will protrude laterally beyond the outer wall of distal end 41 of cannula sleeve 40 when stabilizer 80 is in its undeformed state.

As best shown in FIGS. 13 and 7, as obturator 60 is urged downwardly towards stabilizer 80, distal end portion 64 of obturator 60 will bear against mounting arms 81 and eventually the interior of stabilizer 80. In this manner, distal end portion 64 will provide a deformation force corresponding to force F shown in FIGS. 2 and 4. In fact, even the force imparted against mounting arms 81 above stabilizer 80 by distal end portion 64 will cause stabilizer 80 to begin to deform since mounting arms 81 are attached to stabilizer 80. Thus, as obturator 60 is urged downwardly, distal end portion 64 will cause obturator 80 to resiliently flex to its deformed (or first) position of FIGS. 3 and 5. This allows cutting blade 62 and at least part of distal end portion 64 of obturator 60 to pass through the interior of stabilizer 80 (as best seen in FIGS. 7, 15 and 23), thereby exposing cutting blade 62. With reference to FIG. 5, it will therefore be apparent that stabilizer 80 should be sized such that when stabilizer 80 is in its deformed state, its diameter along any axis should preferably be substantially equal to or less than the diameter of distal end 41 of cannula 40 along a corresponding axis (i.e., an axis parallel to that used to measure the diameter of stabilizer 80). In other words, when stabilizer 80 is in its deformed state, no portion of stabilizer 80 should substantially extend beyond the outer circumference of distal end 41 of sleeve 40. In addition, stabilizer 80 should be dimensioned such that distal end portion 64 of obturator 60 may freely pass through the interior of stabilizer 80, as shown in FIG. 7.

As seen in FIG. 17, as obturator 60 is withdrawn from cannula sleeve 40, distal end portion 64 of obturator 60 will no longer provide a deforming force against the interior of stabilizer 80. Thus, as obturator 60 is withdrawn from cannula sleeve 40, stabilizer 80 will return to its undeformed (or second) position. When this occurs, the location of the maximum diameter across stabilizer 80 will no longer be aligned with the axis defining the maximum cross-sectional diameter of distal end 41 of cannula sleeve 40. In other words, stabilizer 80 will protrude beyond the outer circumference of distal end 41 of cannula sleeve 40, as shown in FIG. 1. In this manner, stabilizer 80 acts as an internal (i.e., within the anatomical cavity) stabilizer which prevents cannula 40 from being withdrawn from the tissue opening.

Figure 16:
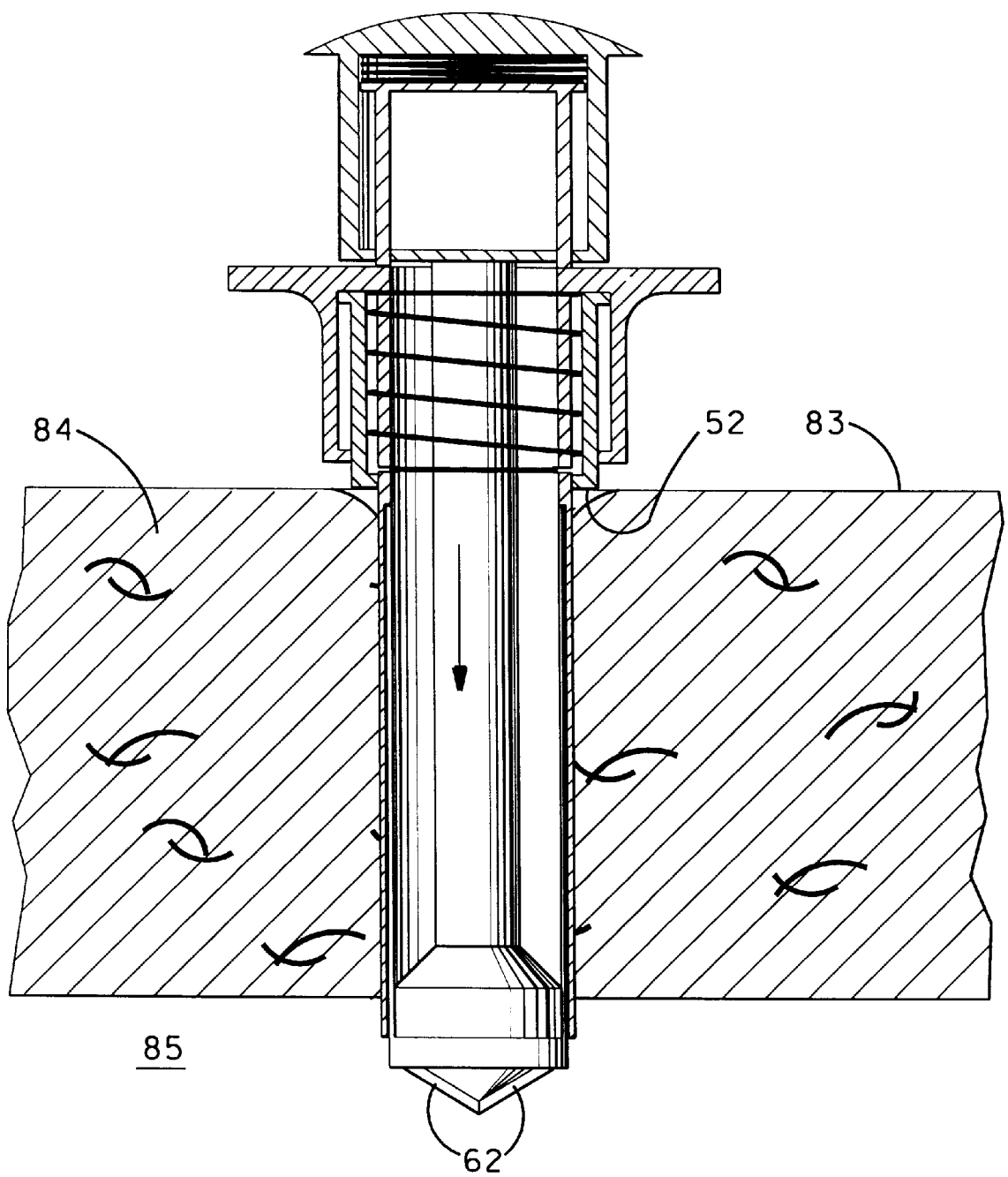
FIG. 16 is the same view as FIG. 15, wherein the cutting blade and cannula sleeve have been urged through a tissue wall into an underlying anatomical cavity.
Figure 20:
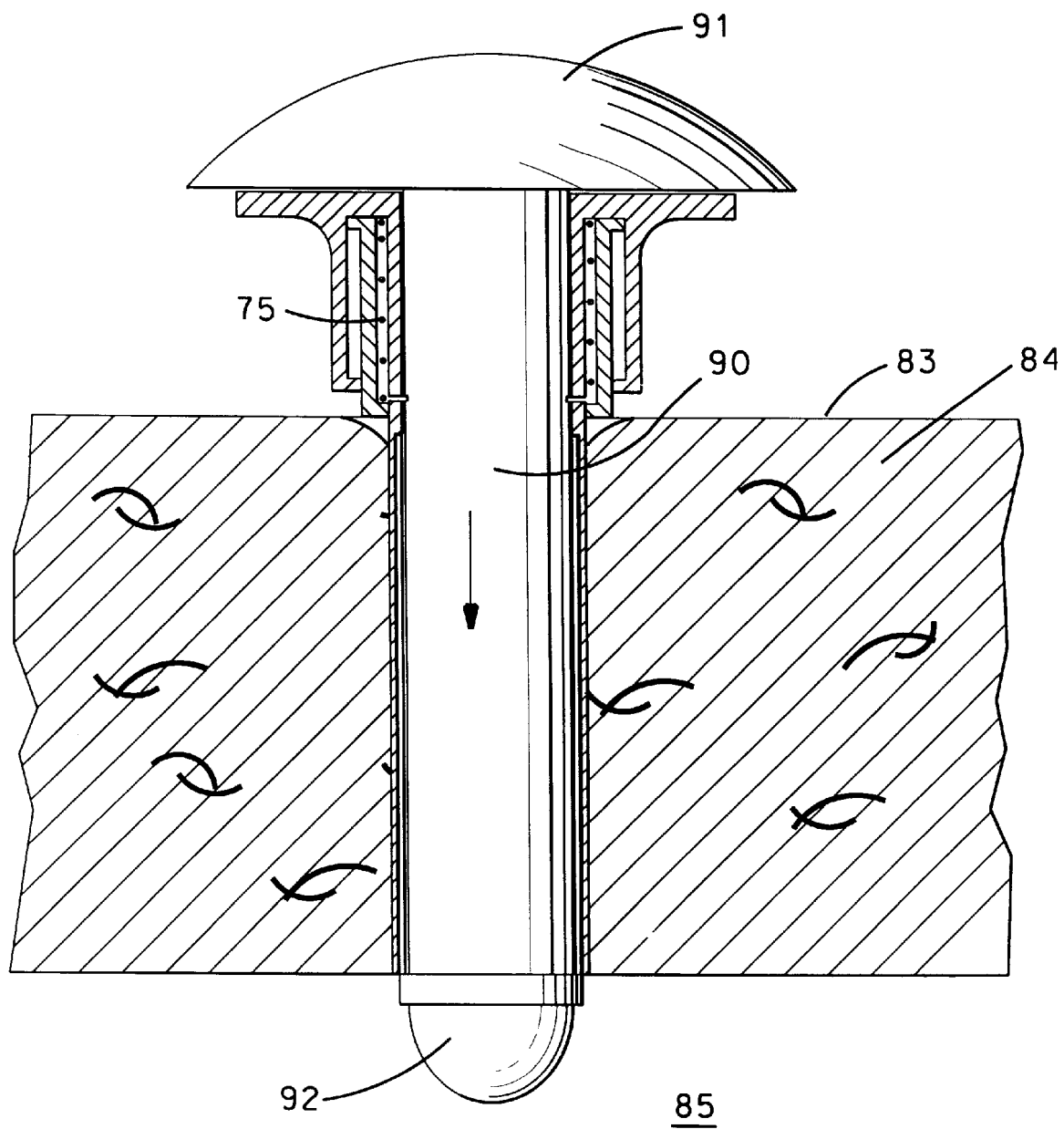
FIG. 20 is the same view as FIG. 19 (with spring 75 shown in cross-section), wherein the cannula release member has been inserted through the cannula sleeve in order to allow for removal of the cannula assembly.

In order to remove the cannula from the tissue opening, the deformation of stabilizer 80 is essentially repeated. Thus, a means for redeforming stabilizer 80 to its position shown in FIGS. 3 and 16. Although obturator 60 could be re-inserted into the cannula to accomplish this, such a procedure would place the patient at risk of injury from the cutting blade of the obturator. Thus, as shown in FIG. 20, a release member 90 is provided. Release member 90 essentially comprises an elongate rod having a blunt tip 92 at one end, and a handle portion 91 at its opposite end. Handle portion 91 should be sized and configured to allow for easy manipulation, as well as to prevent over insertion of release member 90. At least the distal end portion (i.e., that portion adjacent blunt tip 92) of release member 90 should have a cross-sectional size and shape which is slightly less than the interior dimensions of cannula sleeve 40. In this manner, as release member 90 is urged downwardly through the interior of cannula sleeve 40, its distal end portion will bear against mounting arms 81 of stabilizer 80, as well as the interior of stabilizer 80 itself, thereby providing deformation force F shown in FIG. 2. When release member 90 is urged downwardly to its full extent, its distal end portion will cause stabilizer 80 to move to its fully deformed condition (FIG. 3) wherein its exterior dimensions are substantially equal to or less than that of distal end 41 of cannula sleeve 40. In this manner, cannula 40 may then be removed from the tissue opening without interference from stabilizer 80.

Figure 9:
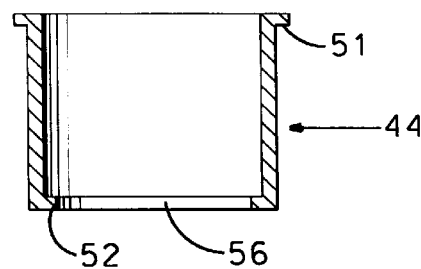
FIG. 9 is a cross-sectional view of the lower housing.

The trocar assembly of the present invention also includes an "upper stabilizer" which is positioned on the opposite side of the tissue wall from stabilizer 80 (typically, against the patient's skin 83). As best seen in FIG. 1, this upper stabilizer comprises a spring-loaded lower housing 44 which is positioned at least partially within upper housing 45. Lower housing 44 comprises a cup-like member (FIG. 9) having a flange 51 about its upper edge, and a bore 56 in its bottom wall 52. Bore 56 is sized to slidingly receive cannula sleeve 40 therein. As best seen in FIG. 13, lower housing 44 is slidably positioned within cavity 46 of upper housing 45, with a portion of lower housing 44 preferably extending beyond inner lip 48 on upper housing 45. Lower housing 44 is free to slide downwardly towards distal end 41 of cannula sleeve 40, however the extent of downward movement is limited by flange 51 of lower housing 44 bearing against inner lip 48 of upper housing 45.

Figure 10:
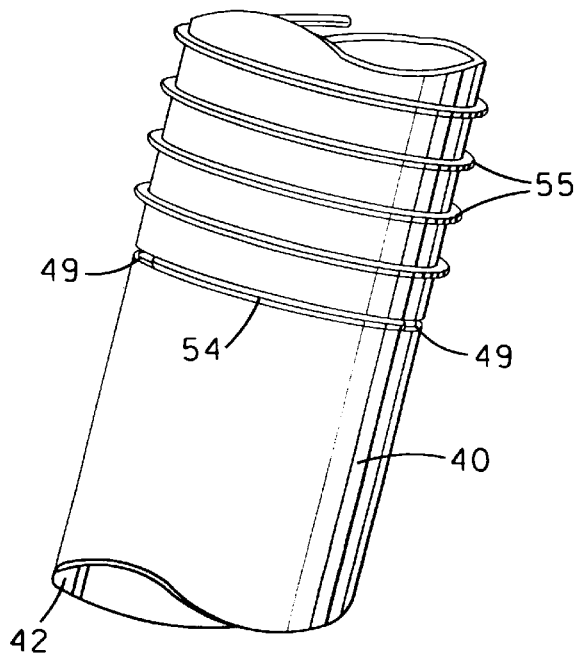
FIG. 10 is a perspective view of a portion of the cannula sleeve and housing spring of the present invention.

Lower housing 44 is also spring-biased towards distal end 41 of cannula sleeve 40, however this spring-biasing is normally deactivated as long as obturator 60 remains substantially within sleeve 40. This selective spring-biasing is provided by helical housing spring 53 which is shown in FIGS. 10 and 11. Helical housing spring 53 preferably has a circular lower revolution 54, and a plurality of elliptical upper revolutions 55. Elliptical upper revolutions 55 are sized such that helical housing spring 53 may extend about the circumference of cannula sleeve 40, as best shown in FIG. 10.

Cannula sleeve 40 has a pair of notches 40 positioned on opposite sides thereof, above cutouts 42. Notches 49 extend to the interior of cannula sleeve 40, as best seen in FIG. 8. Lower circular revolution 54 of housing spring 53 extends about the circumference of cannula sleeve 40 and through each notch 49, as shown in FIG. 10, such that a portion of lower revolution 54 protrudes into the interior of sleeve 40. It should be noted that lower revolution 54 of spring 53 may, in addition to being circular, comprise an elliptical shape which is less oblong than upper revolutions 55. In any event, lower revolution 54 of spring 53 is positioned within notches 49 such that lower revolution 54 extends into the interior of cannula sleeve 40.

Since shaft 61 of obturator 60 has a diameter significantly smaller than the interior diameter of cannula shaft 40, lower revolution 54 of housing spring 53 will not interfere with passage of shaft 61. When obturator 60 is removed from cannula sleeve 40, however, conical taper portion 65 of distal end portion 64 of the obturator will be urged against those portions of lower revolution 54 of spring 53 which extends through notches 49 into the interior of the cannula sleeve. Thus, as shown in FIG. 18, as conical taper portion 65 is withdrawn past lower revolution 54 of housing spring 53, the tapered walls will urge lower revolution 54 out of notches 49. When this occurs, helical spring 53 is released and will bear against bottom wall 52 of lower housing 44 thereby urging bottom wall 52 towards the patient's skin surrounding the tissue opening. Simultaneously, housing spring 53 will also bear against upper wall 50 of upper housing 45. Since upper housing 45 is attached to cannula sleeve 40, the upper force provided by housing spring 53 will, in turn, urge cannula sleeve 40 (and hence stabilizer 80) upwardly. Stabilizer 80 (in its undeformed state) limits the upward movement of cannula sleeve 40, and therefore cannula sleeve 40 is urged upwardly until stabilizer 80 bears against the interior surface 86 of tissue wall 84 surrounding the opening through which cannula sleeve 40 has passed. In general, distal end 41 of cannula sleeve 40 will therefore be located substantially coextensive with interior surface 86 of tissue wall 84, as shown in FIG. 18. The trocar of the present invention thus provides both upper and lower stabilizers which are spring-biased towards one another. In this manner, the tissue wall surrounding the opening through which cannula sleeve 40 is positioned will essentially be compressed between housing 44 and stabilizer 80, thereby insuring that cannula sleeve 40 will not become dislodged.

Figure 24:
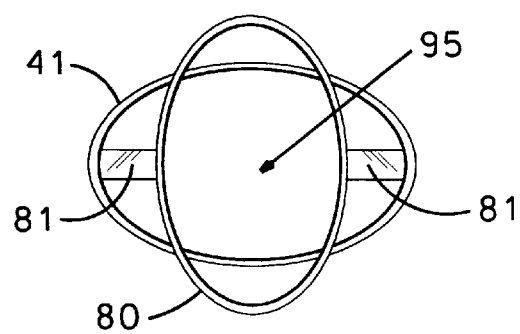
FIG. 24 is an end view of the trocar assembly of FIG. 19.

As best seen in FIG. 24, when the preferred elliptical cross-sectional shapes are employed for cannula sleeve 40 and stabilizer 80, a marquise-shaped opening 95 is provided at the lower end of the device of the present invention. Marquise-opening 95 can readily accommodate endoscopes and other surgical instruments currently used through trocar cannulas, since such instruments are typically circular in cross-sectional shape. As long as the diameter of distal end 41 of cannula sleeve 40 and stabilizer 80 along each of their minor axis is slightly greater than the maximum cross-sectional diameter of the surgical instrument, such instrument can be readily employed through the trocar cannula of the present invention.

The foregoing description of preferred embodiments is by no means exhaustive of the possible variations of the present invention, and has therefore been provided only for purposes of illustration and description. Modifications, variations and additions to the foregoing specific examples will be readily apparent to those skilled in the art in light of the teachings provided above, and are all well within the scope of the present invention. For example, various additional features commonly found on trocars may be included on the trocar assembly of the present invention. For example, the cannula various internal valve systems (such as a flapper valve) for maintaining a gas tight seal within the cannula. Such valves are shown, for example, in U.S. Pat. Nos. 5,454,791 and 5,379,625. In addition, stopcock valves and other ports may also be provided on the cannula sleeve and/or either housing, as is well-known to those skilled in the art (and as shown, for example, in U.S. Pat. No. 5,454,791. In addition, various types of safety shields may also be included, such as that shown in U.S. Pat. No. 5,215,526. Furthermore, the elliptical shape for stabilizer 80 is but merely one preferred embodiment, and it will be understood that other shapes (particularly other non-circular shapes) may be employed without departing from the scope of the present invention, particularly if the particular shape can be readily deformed from a cannula retaining to a cannula passing configuration (and back again). In the retaining (i.e., non-deformed state) at least a portion of the stabilizer extends beyond the outer circumference of the distal end of the cannula sleeve, while in its passing (or deformed) state it does not. Thus, it is intended that the scope of the present invention be defined by the claims provided below, and not by any of the specific embodiments shown in the drawings and/or described above.

What we claim is:

1. A method of inserting a cannula through a tissue wall into an anatomical cavity, comprising:

(a) providing a trocar having a cannula and an obturator, said cannula having:
    a sleeve having a distal end and a longitudinal axis; and
    a stabilizer positioned adjacent the distal end of said sleeve, said stabilizer movable between extended and retracted positions;
    said obturator positioned at least partially within said sleeve, and having a distal end configured for penetrating tissue;

(b) positioning the distal end of said obturator adjacent a tissue wall to be penetrated;

(c) advancing the distal end of said obturator and said cannula sleeve through said tissue wall into said anatomical cavity, with said distal end of the obturator extending beyond the distal end of said sleeve and said stabilizer maintained in said retracted position by said obturator; and (d) withdrawing said obturator away from the distal end of said sleeve, said withdrawal causing said stabilizer to move from said retracted position to said extended position, such that said stabilizer prevents removal of said cannula from the anatomical cavity.

2. The method of claim 1, wherein when said stabilizer is in its extended position, at least a portion of said stabilizer extends beyond the outer circumference of said distal end of said cannula sleeve.

3. The method of claim 2, wherein when said stabilizer is in its retracted position, said stabilizer does not extend substantially beyond the outer circumference of said distal end of said cannula sleeve.

4. The method of claim 1, wherein said cannula further comprises a spring-biased retention member spaced away from the distal end of said cannula sleeve, said retention member spring-biased towards the distal end of said cannula sleeve.

5. The method of claim 4, wherein said retention member is selectively spring-biased such that said spring-biasing is activated only upon withdrawal of said obturator away from the distal end of said sleeve.

6. The method of claim 5, wherein said retention member, is configured such that, upon activation of said spring-biasing, the retention member is urged against the exterior of the tissue wall through which said cannula is inserted.

7. The method of claim 6, wherein said stabilizer comprises an elliptical member which extends away from the distal end of said sleeve,.

8. A trocar comprising:
    a cannula having a distal end, a first stabilizer positioned adjacent the distal end of said cannula, and a spring-biased second stabilizer spaced away from said distal end; wherein said cannula may be inserted through a tissue wall in order to provide operative access to an underlying anatomical cavity, with said first stabilizer positioned adjacent said tissue wall within the anatomical cavity and said second stabilizer spring-biased against the tissue wall outside of said anatomical cavity.

9. The trocar of claim 8, further comprising an obturator slidably disposed at least partially within said cannula and having a distal end configured for penetrating a tissue wall.

10. The trocar of claim 9, configured such that advancement of said obturator towards the distal end of said cannula deforms said first stabilizer to a retracted position which facilitates passage of the distal end of the cannula through a tissue wall.

11. The trocar of claim 10, configured such that withdrawal of said obturator away from the distal end of said cannula allows said first stabilizer to return to its extended, undeformed position which prevents removal of the cannula from a tissue wall through which it extends.

12. The trocar of claim 9, wherein said first stabilizer is configured such that the distal end of said obturator may be advanced through the interior of said first stabilizer.

13. The trocar of claim 8, wherein said second stabilizer is selectively spring-biased, and said trocar is configured such that withdrawal of said obturator away from the distal end of said cannula activates said spring-biasing thereby urging said second stabilizer towards the distal end of said cannula.

14. The trocar of claim 8, wherein said first stabilizer comprises an eliptical member, wherein said eliptical member is configured such that it may be moved to said retracted position by deforming said eliptical member.

15. The trocar of claim 8, wherein said first stabilizer extends beyond the distal end of said cannula.

16. A method of inserting a cannula through a tissue wall, comprising:
   (a) providing a trocar having a cannula and an obturator, said cannula having:
      a sleeve having a distal end;
      a stabilizer positioned adjacent the distal end of said sleeve, said stabilizer movable between extended and retracted positions; and
      a retention member spaced away from said stabilizer and the distal end of said sleeve;
      said obturator positioned at least partially within said sleeve, and having
      a distal end;
   (b) advancing the distal end of said obturator and the distal end of said cannula sleeve through said tissue wall with said stabilizer in said retracted position;
   (c) causing said stabilizer to move from said retracted position to said extended position, such that said stabilizer prevents removal of said cannula from the tissue wall; and
   (d) urging said retention member against the exterior of the tissue wall through which said cannula is inserted.

17. The method of claim 16, wherein said retention member is spring-biased towards the distal end of said cannula sleeve.

18. The method of claim 17, further comprising the step of withdrawing said obturator away from the distal end of said cannula sleeve, said withdrawal causing said stabilizer to move from said retracted position to said extended position.

19. The method of claim 18, wherein said retention member is selectively spring-biased such that withdrawal of said obturator away from the distal end of said cannula activates said spring-biasing thereby urging said retention member against the exterior of the tissue wall.

20. The method of claim 16, further comprising the step of causing said stabilizer to move from said extended position to said retracted position, and thereafter removing said cannula from the tissue wall.

21. The method of claim 20, further comprising the step of inserting a release member into said cannula sleeve and urging said release member towards the distal end of the cannula sleeve, said release member causing said stabilizer to move from said extended position to said retracted position.

* * * * *